(12) United States Patent
Kondo et al.

(10) Patent No.: US 10,980,939 B2
(45) Date of Patent: Apr. 20, 2021

(54) MEDICINAL-LIQUID ADMINISTERING DEVICE

(71) Applicant: TERUMO KABUSHIKI KAISHA, Tokyo (JP)

(72) Inventors: Akira Kondo, Numazu (JP); Joji Uchiyama, Hadano (JP); Hideyuki Sato, Sendai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/840,722

(22) Filed: Apr. 6, 2020

(65) Prior Publication Data

US 2020/0230314 A1 Jul. 23, 2020

Related U.S. Application Data

(60) Division of application No. 15/922,458, filed on Mar. 15, 2018, now Pat. No. 10,646,642, which is a (Continued)

(30) Foreign Application Priority Data

Sep. 25, 2015 (JP) .............................. JP2015-188283

(51) Int. Cl.
*A61M 5/142* (2006.01)
*A61M 5/145* (2006.01)
*A61M 5/14* (2006.01)

(52) U.S. Cl.
CPC ........ *A61M 5/14248* (2013.01); *A61M 5/142* (2013.01); *A61M 5/145* (2013.01); *A61M 5/1413* (2013.01); *A61M 2005/14268* (2013.01)

(58) Field of Classification Search
CPC .. A61M 5/14248; A61M 5/142; A61M 5/145; A61M 2005/14268; A61M 5/1456;
(Continued)

(56) References Cited

U.S. PATENT DOCUMENTS 8,157,769 B2 * 4/2012 Cabiri ............... A61M 5/14248
604/151
2009/0093793 A1 * 4/2009 Gross ...................... F16H 25/12
604/518

(Continued)

FOREIGN PATENT DOCUMENTS

JP 2008-246987 A 10/2008
JP 2010-535057 A 11/2010
(Continued)

OTHER PUBLICATIONS

International Searching Authority, "International Search Report," issued in connection with International Patent Application No. PCT/JP2016/077715, dated Dec. 20, 2016.
(Continued)

*Primary Examiner* — Theodore J Stigell
*Assistant Examiner* — Rachel T. Smith
(74) *Attorney, Agent, or Firm* — Foley & Lardner LLP (57) ABSTRACT

A device includes: a first member comprising a first-member-side power transmission part; and a second member comprising a second-member-side power transmission part configured to be attachable to and detachable from the first member, the second member being a part of a medicinal-liquid administering device. The first-member-side power transmission part and the second-member-side power transmission part are configured to be engaged with each other for administering a medicinal liquid into a living body. The second member is configured to open a housing covering the first-member-side power transmission part to engage the
(Continued)

second-member-side power transmission part with the first-member-side power transmission part at a time of attaching the first member to the second member.

22 Claims, 7 Drawing Sheets

Related U.S. Application Data continuation of application No. PCT/JP2016/077715, filed on Sep. 20, 2016.

(58) Field of Classification Search
CPC .............. A61M 5/158; A61M 5/14268; A61M 2005/14573; A61M 5/1413; A61M 2205/12; A61M 2205/121; A61M 2205/122; A61M 5/14228; A61M 5/14232
See application file for complete search history.

(56) References Cited

U.S. PATENT DOCUMENTS

| | | |
|---|---|---|
| 2009/0221964 A1 | 9/2009 | Rotem et al. |
| 2011/0213329 A1 | 9/2011 | Yodfat et al. |
| 2015/0157537 A1* | 6/2015 | Lanigan .................. B65B 3/003 |
| | | 141/349 |

FOREIGN PATENT DOCUMENTS

| | | |
|---|---|---|
| JP | 2013-504405 A | 2/2013 |
| JP | 2013-516231 A | 5/2013 |

OTHER PUBLICATIONS

International Searching Authority, "Written Opinion," issued in connection with International Patent Application No. PCT/JP2016/077715, dated Dec. 20, 2016.

\* cited by examiner

MEDICINAL-LIQUID ADMINISTERING DEVICE

CROSS-REFERENCE TO RELATED APPLICATIONS

The present application is a divisional of U.S. patent application Ser. No. 15/922,458, filed on Mar. 15, 2018, which is a bypass continuation of PCT Application No. PCT/JP2016/077715, filed on Sep. 20, 2016, which claims priority to Japanese Application No. 2015-188283, filed on Sep. 25, 2015. The contents of these applications are hereby incorporated by reference in their entireties.

BACKGROUND

The present disclosure relates to a portable medicinal-liquid administering device that continuously or intermittently administers medicinal liquid filled in a medicinal liquid container into a living body by pressing a pressing member, which is operated by driving force from a driving source, toward the medicinal liquid.

For example, JP 2010-535057 A discloses a medicinal-liquid administering device in FIGS. 17a and 17b, which includes a reusable part, and a disposable part that is attachable to and detachable from the reusable part. The reusable part of the medicinal-liquid administering device includes a reusable-side threaded part to which driving force from a driving source is transmitted. The disposable part includes a disposable-side threaded part that meshes with the reusable-side threaded part when the disposable part is attached to the reusable part, and transmits, to a plunger rod, the driving force transmitted from the driving source to the reusable-side threaded part.

SUMMARY

However, because the medicinal-liquid administering device described above is configured such that a reusable-side power transmission part (reusable-side threaded part) is exposed outward when the disposable part is unattached to the reusable part, foreign matter such as grit and dust may adhere to the reusable-side power transmission part. With the foreign matter adhered to the reusable-side power transmission part, the driving force from the driving source may fail to be transmitted to a pressing member (plunger rod) effectively.

Certain embodiments described herein have been developed in consideration of such a problem, and it is one object of certain embodiments to provide a medicinal-liquid administering device configured to inhibit adhesion of foreign matter onto the reusable-side power transmission part when the disposable part is unattached to the reusable part.

In one embodiment, a medicinal-liquid administering device is a portable medicinal-liquid administering device for continuously or intermittently administering medicinal liquid filling a medicinal liquid container into a living body by pressing, toward the medicinal liquid, a pressing member to be operated by driving force from a driving source, the medicinal-liquid administering device including: a reusable part that is reusable; and a disposable part that is provided to be attachable/detachable to/from the reusable part and is disposable, wherein the reusable part includes: the driving source; a reusable-side power transmission part to which the driving force from the driving source is transmitted; a housing that houses the reusable-side power transmission part and is provided with an opening part partially exposing the reusable-side power transmission part; an openable/closable cover part provided at the opening part of the housing; and a pushing member that pushes the cover part into a closed state, the disposable part includes: the medicinal liquid container; the pressing member; a disposable-side power transmission part that engages with the reusable-side power transmission part upon attachment of the reusable part and the disposable part and transmits, to the pressing member, the driving force transmitted from the driving source to the reusable-side power transmission part; and a contact part capable of contacting the cover part, and the cover part contacts the contact part to be opened and maintained in an opened state while resisting pushing force of the pushing member when the disposable part is attached to the reusable part, and the cover part is closed to block the opening part by the pushing force of the pushing member when the disposable part is detached from the reusable part.

According to such a configuration, because the openable/closable cover part is provided at the opening part of the housing that houses the reusable-side power transmission part, adhesion of foreign matter onto the reusable-side power transmission part can be inhibited when the disposable part is unattached to the reusable part. Moreover, at the time of attaching the disposable part to the reusable part, the cover part contacts the contact part to be opened while resisting the pushing force of the pushing member, and maintains the opened state. Accordingly, a user is not required to hold the cover part in the opened state with fingers or the like, when attaching the reusable part to the disposable part. The disposable-side power transmission part can be therefore easily and securely engaged with the reusable-side power transmission part without the need of complicated work. Furthermore, because the cover part is automatically closed by the pushing force of the pushing member when the disposable part is detached from the reusable part, the user is not required to close the cover part with fingers or the like. Therefore, adhesion of foreign matter onto the reusable-side power transmission part can be inhibited without the need of a complicated procedure.

In the medicinal-liquid administering device described above, the cover part may be rotatably mounted on the housing via a shaft. The pushing member may push the cover part into the closed state by applying the pushing force to the cover part along a circumferential direction of the shaft.

According to such a configuration, it becomes possible to push the cover part into the closed state with a simple configuration.

In the medicinal-liquid administering device described above, the reusable-side power transmission part may include an output gear that rotates by the driving force from the driving source. The output gear may be partially exposed outside of the housing via the opening part when the cover part is in the opened state. The disposable-side power transmission part may include an input gear that can mesh with the output gear.

According to such a configuration, the driving force of the reusable-side power transmission part can be transmitted to the disposable-side power transmission part effectively by the input gear meshing with the output gear.

In the medicinal-liquid administering device described above, the reusable part may include an attachment part to which the housing is attached and that covers the disposable part. The shaft may be located on the side closer to the attachment part than the opening part. The cover part may open toward the attachment part side when the disposable part is attached to the reusable part.

According to such a configuration, the cover part can be securely opened when the disposable part is attached to the reusable part.

In the medicinal-liquid administering device described above, an axis of the shaft may be located at, in an aligning direction in which the output gear and the input gear align in the attached state, the same position as the rotation axis of the output gear or the side opposite to the side where the input gear is located in the attached state with respect to the rotation axis of the output gear. A portion of the cover part that contacts the contact part first when the disposable part is attached to the reusable part may be located on, in the aligning direction, the same side where the input gear is located in the attached state with respect to the rotation axis of the output gear.

According to such a configuration, the cover part can be easily opened at the time of attaching the disposable part to the reusable part.

In the medicinal-liquid administering device described above, the disposable-side power transmission part includes a rotation shaft that is coaxially provided relative to the input gear and a bearing that rotatably supports the rotation shaft. The contact part may be provided on the bearing.

According to such a configuration, the disposable part can be simply configured.

In the medicinal-liquid administering device described above, the pushing member may be a torsion spring that includes a coil and a pair of extended end parts extending from the coil. The shaft may be provided in an internal hole of the coil. One of the extended end parts may be locked to the housing. The other one of the extended end parts may be locked to the cover part.

According to such a configuration, the pushing member can be simply configured.

In the medicinal-liquid administering device described above, the cover part may be pushed onto the wall surface of the housing by the pushing force of the pushing member, when the cover part is in the closed state.

According to such a configuration, adhesion of foreign matter onto the reusable-side power transmission part can be securely inhibited.

According to certain embodiment described herein, because the openable/closable cover part is provided at the opening part of the housing that houses the reusable-side power transmission part, adhesion of foreign matter onto the reusable-side power transmission part can be inhibited when the disposable part is unattached to the reusable part.

DETAILED DESCRIPTION

Hereinafter, a medicinal-liquid administering device according to certain embodiments will be described with a suitable embodiment with reference to the attached drawings.

Figure 1:
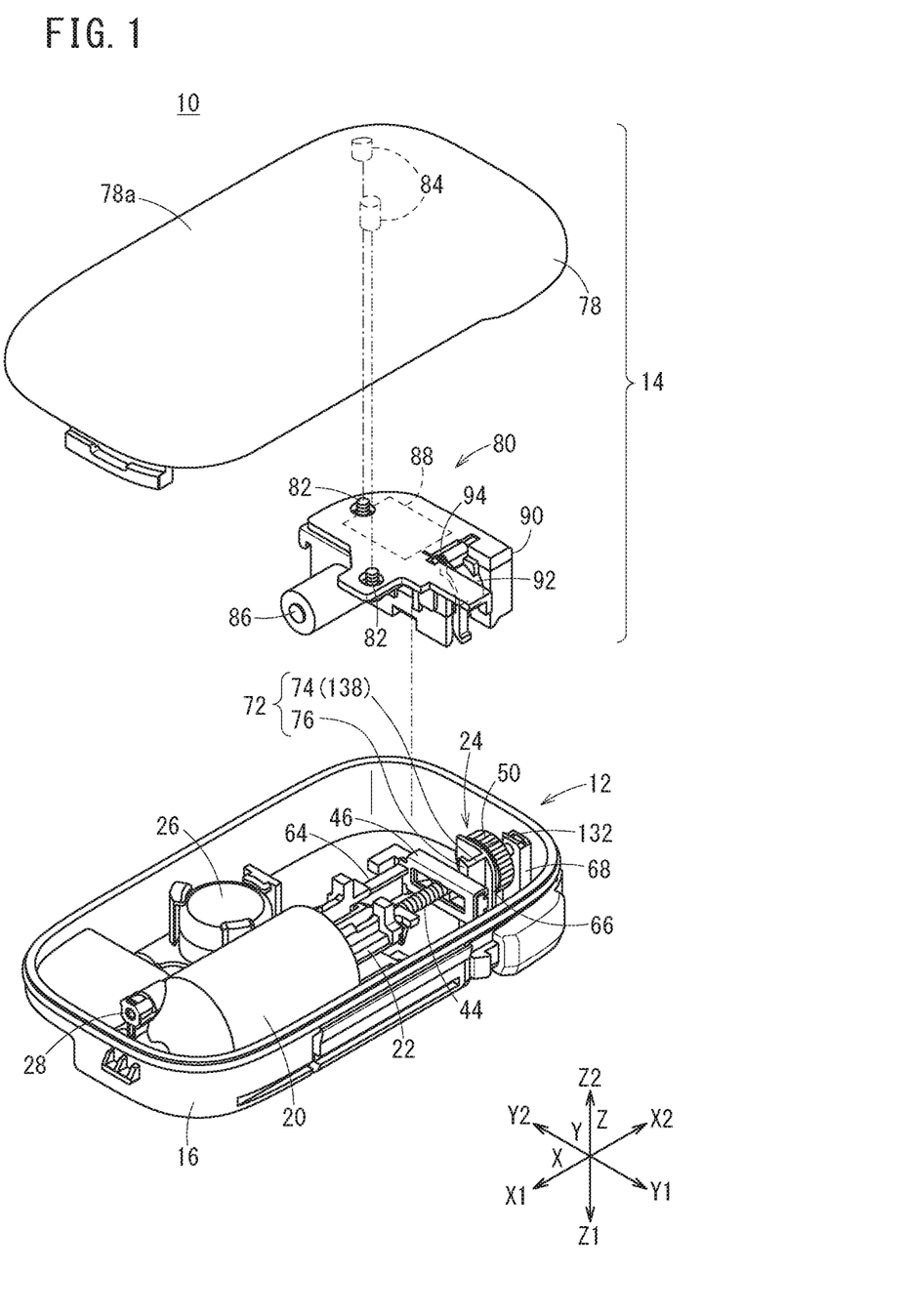
FIG. 1 is an exploded perspective view of a medicinal-liquid administering device according to one embodiment.

As shown in FIG. 1, a medicinal-liquid administering device 10 according to the present embodiment is a portable medicinal-liquid administering device 10 that continuously or intermittently administers medicinal liquid, which fills a tubular body 20, into a living body under a pressing action of a plunger 22. The medicinal-liquid administering device 10 is configured as a patch-type insulin pump. However, the medicinal-liquid administering device 10 is not limited to the patch type, but may be a tube type or the like.

The medicinal-liquid administering device 10 includes a disposable part 12 that is disposable, and a reusable part 14 that is reusable. The disposable part 12 includes a base part (disposable part main body) 16 having a flat-box shape with one side (Z2 direction) opened. The base part 16 is substantially rectangular in planar view, and is attachable/detachable to/from a cradle (not shown). Note that the cradle is a holder (holding member), which can be pasted onto the skin of a user (patient).

Figure 2:
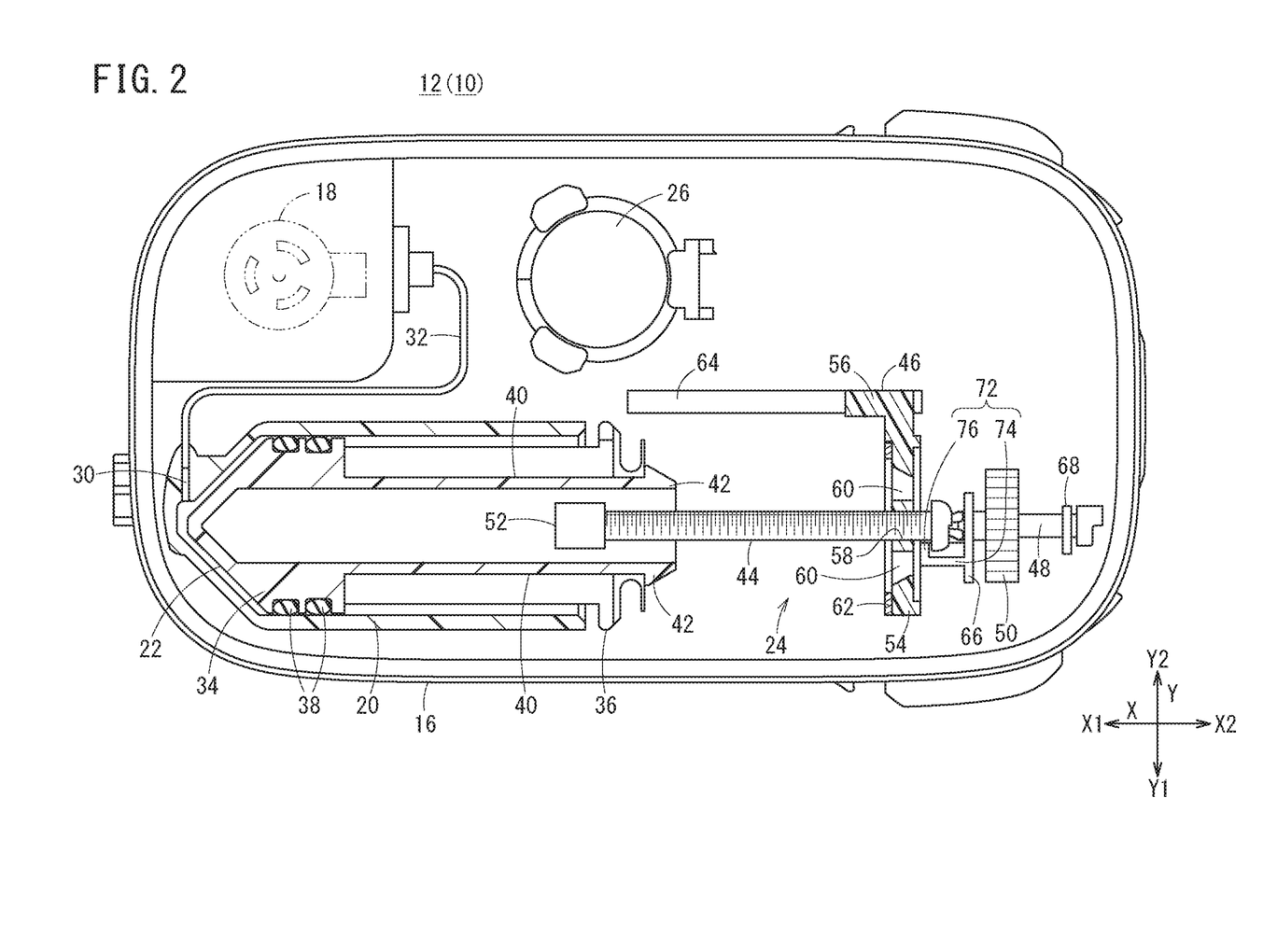
FIG. 2 is a partial cross-sectional plan view of a disposable part of FIG. 1.

As shown in FIG. 2, the cradle like this is provided with a cannula mechanism 18 having a cannula. The cannula mechanism 18 is unattached to the cradle in the initial state, while being supported by a needling mechanism (not shown). When the needling mechanism is operated, the cannula mechanism 18 including the cannula moves toward the living body, whereby the cannula punctures the living body and the cannula mechanism 18 is fixed (attached) to the cradle.

The disposable part 12 includes a tubular body (medicinal liquid container) 20 to be filled with medicinal liquid, a plunger (pressing member) 22 provided in the tubular body 20, a disposable-side power transmission part 24, and a battery 26.

The tubular body 20 is provided on the base part 16, extending in a cylindrical shape along a longitudinal direction (X direction) of the base part 16. The outer diameter and the inner diameter of a distal-end part (X1-direction end part) of the tubular body 20 are reduced toward a distal end. At the distal-end part of the tubular body 20 like this, a lead-in port 28 (see FIG. 1) for leading the medicinal liquid into the tubular body 20 and a lead-out port 30 for leading the medicinal liquid out from the tubular body 20 are formed. A lumen of a lead-out tube 32, which leads the medicinal liquid in the tubular body 20 to the cannula, communicates with the lead-out port 30.

The plunger 22 is integrally molded by using a resin material or the like and is provided in the tubular body 20 to be liquid-tightly slidable along the axis direction of the tubular body 20. The plunger 22 includes a plunger main body 34, which constitutes a distal-end side, and a pusher 36, which is provided on the plunger main body 34 and constitutes a rear-end side. A pair of packings 38 is attached to the cylindrical rear-end side of the plunger main body 34.

The pusher 36 includes a pair of leg parts 40 extending rearward (X2 direction) from the plunger main body 34 to the outside of the tubular body 20, and a pair of claw parts 42 provided at rear-end parts of the leg parts 40. The leg parts 40 are provided along a short-side direction (Y direction) of the base part 16 while being spaced apart from each other.

The disposable-side power transmission part 24 includes a feed screw shaft 44 coaxially disposed with respect to the plunger 22, a nut part 46 screwed together with the feed screw shaft 44, a rotation shaft 48 integrally rotatably locked to the feed screw shaft 44, and a input gear 50 secured to the rotation shaft 48. One end part (X1-direction end part) of the feed screw shaft 44 is pivotally supported by a bearing 52.

The nut part 46 is integrally molded by using a resin material or the like and includes a nut-part main body 54 formed in substantially a rectangular parallelepiped shape and a slide part 56 provided in the nut-part main body 54. In the nut-part main body 54, a screw hole 58 and a pair of through holes 60 are provided. The screw hole 58 is screwed by the feed screw shaft 44. The through holes 60 are formed on both sides of the screw hole 58 in the Y direction, and the claw parts 42 are inserted into the through holes 60. A reinforcing cover 62 formed of, for example, a metal material or the like is attached to the outer surface of the nut part 46.

The slide part 56 slides with respect to a guide wall 64, which is provided on the bottom surface of the base part 16 and is extended along the axis direction of the plunger 22. More specifically, the nut part 46 before use is at an initial position that is not in contact with the plunger 22. The nut part 46 moves from the initial position under a rotary action of the feed screw shaft 44, contacts the plunger 22, and presses the plunger 22 to the distal-end side. Note that FIGS. 1 and 2 show the medicinal-liquid administering device 10 before use.

The rotation shaft 48 is coaxially coupled to the other end (X2-direction end part) of the feed screw shaft 44 to be integrally rotatable. One end of the rotation shaft 48 is pivotally supported by a bearing 66, and the other end of the rotation shaft 48 is pivotally supported by a bearing 68.

Figure 4:
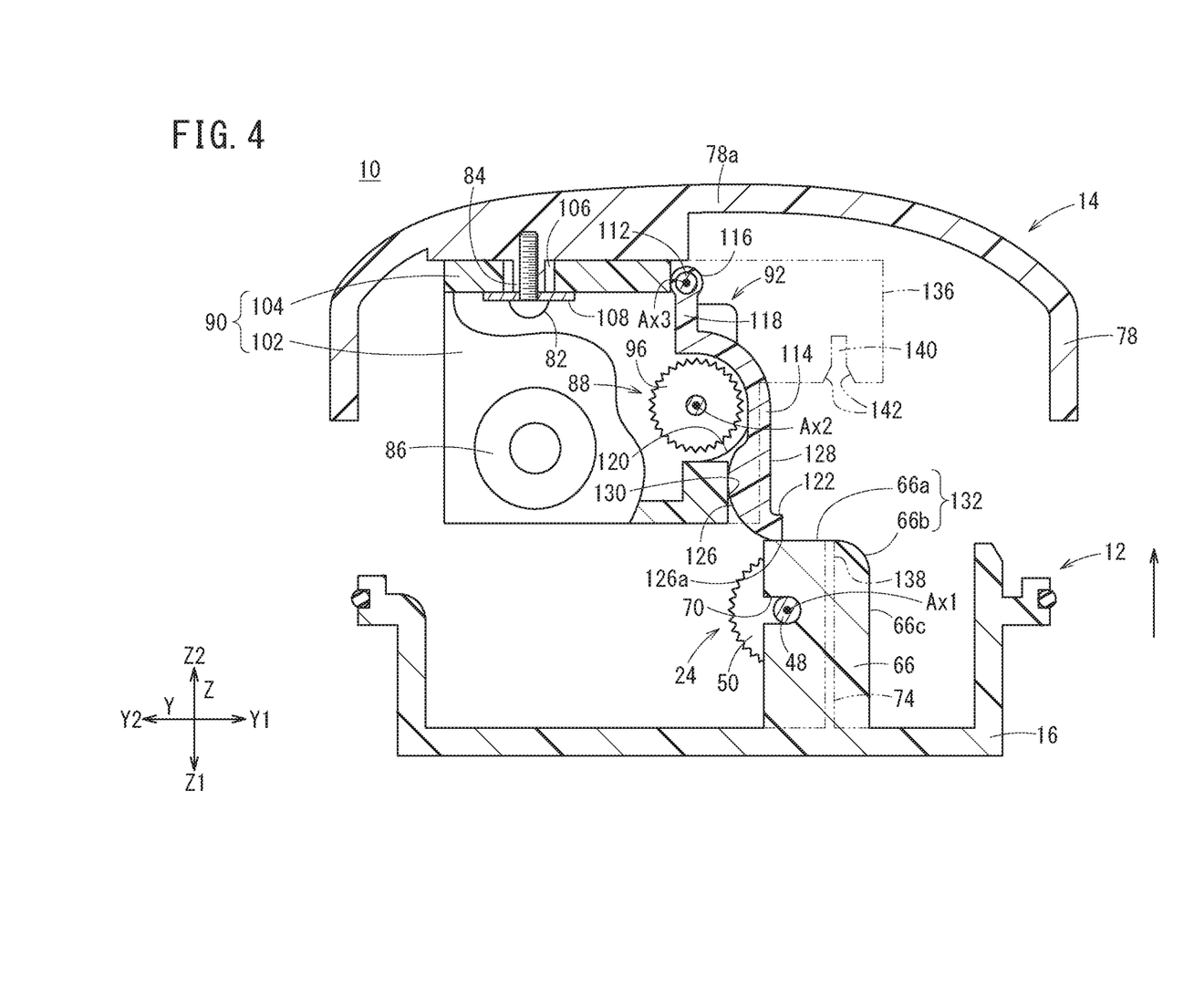
FIG. 4 is a partially omitted cross-sectional view of the cover part contacting a contact part when the disposable part is attached to a reusable part.

As shown in FIG. 4, the bearing 66 is a plate member having substantially a rectangular shape extending in the Z2 direction from the bottom surface of the base part 16. A shaft hole 70, in which the rotation shaft 48 is provided, is formed in the bearing 66 at a position that is slightly shifted in the Z2 direction (side opposite to the bottom surface of the base part 16) from the center in the extended direction (Z direction). The shaft hole 70 passes through both sides of the bearing 66 and opens in the Y2 direction.

A distal-end surface 66a of the bearing 66, which is oriented in the Z2 direction, is located further in the Z2 direction than the input gear 50, while extending substantially in parallel to the bottom surface of the base part 16. Moreover, the distal-end surface 66a is continued to a side surface 66c of the bearing 66, which is oriented in the Y1 direction, via a convex curved surface 66b.

As shown in FIG. 2, the bearing 66 is provided integrally with a rib 72 protruding from the bottom surface of the base part 16 in the Z2 direction. With this configuration, rigidity of the bearing 66 can be increased. The rib 72 is substantially L-shaped in planar view, and includes a first wall 74 extending in the X1 direction from the bearing 66 and a second wall 76 extending in the Y2 direction from the X1-direction end part of the first wall 74. Note that a dimension of the first wall 74 in the Z direction (direction orthogonal to the bottom surface of the base part 16) is set to be substantially the same dimension of the bearing 66 in the Z direction (see FIG. 4).

The input gear 50 has a rotation axis Ax1 along the X direction. The input gear 50 is configured as, but not limited to, a spur gear. In other words, the input gear 50 may be configured as, for example, a helical gear.

As shown in FIG. 1, the reusable part 14 includes a cover body (reusable part main body) 78 attachable/detachable to/from the base part 16, and a driving part 80 formed to be movable along the Y direction with respect to the cover body 78. The cover body 78 is substantially rectangular-shaped in planar view, and attached to the base part 16 such that the opening part of the base part 16, which is oriented in the Z2 direction, is blocked. An attachment part 78a of the cover body 78, which covers the disposable part 12, is provided with a plurality (two in the example of FIG. 1) of bosses 84 screwed by a screw member 82, which is used to attach the driving part 80 to the attachment part 78a.

The driving part 80 includes a motor 86 serving as a driving source, a reusable-side power transmission part 88 to which driving force from the motor 86 is transmitted, a housing (supporting member) 90 for housing the reusable-side power transmission part 88, an openable/closable cover part 92 provided at an opening part 100 (see FIG. 3B) formed on the housing 90, and a pushing member 94 for pushing the cover part 92 into the closed state.

The motor 86 is secured to the housing 90, and can be electrically coupled to the battery 26 when the disposable part 12 is attached to the reusable part 14 (attached state). That is, the motor 86 is driven by power from the battery 26 of the disposable part 12.

Figure 3A:
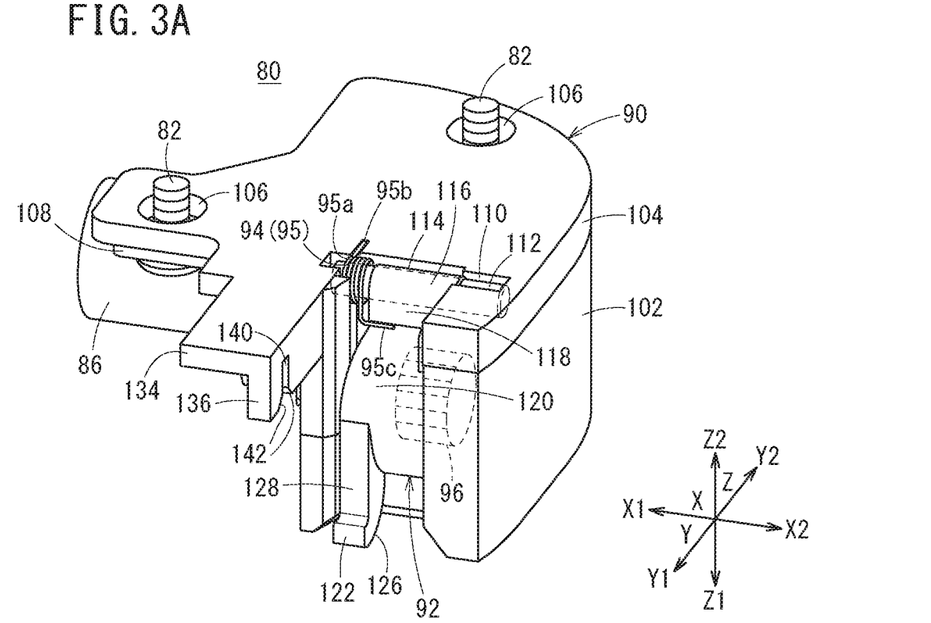
FIG. 3A is an enlarged perspective view of a driving part of FIG. 1.
Figure 3B:
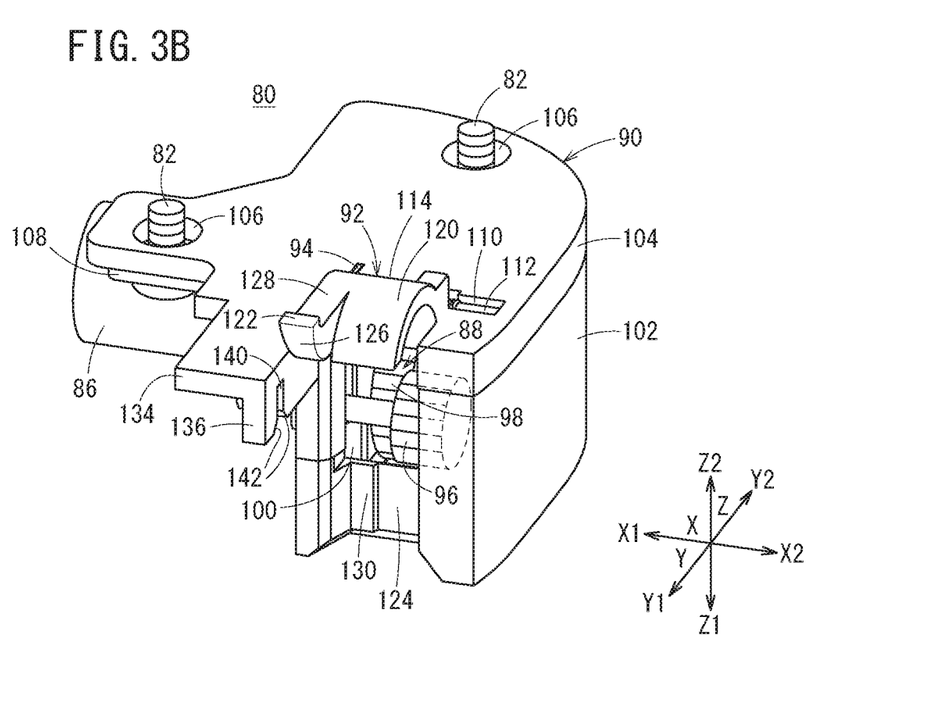
FIG. 3B is an enlarged perspective view of the driving part of FIG. 3A with a cover part opened.

As shown in FIGS. 3A to 4, the reusable-side power transmission part 88 includes an output gear 96 that is meshed (engaged) with the input gear 50 of the disposable-side power transmission part 24 in the attached state. The output gear 96 has a rotation axis Ax2 along the X direction. More specifically, the rotation axis Ax2 of the output gear 96 and the rotation axis Ax1 of the input gear 50 are positioned in parallel in the attached state (see FIG. 7). The output gear 96 is configured as, but not limited to, a spur gear. In other words, the output gear 96 may be configured as, for example, a helical gear. A deceleration mechanism 98 (see FIG. 3B) is provided on the power transmission path between the motor 86 and the output gear 96.

Figure 7:
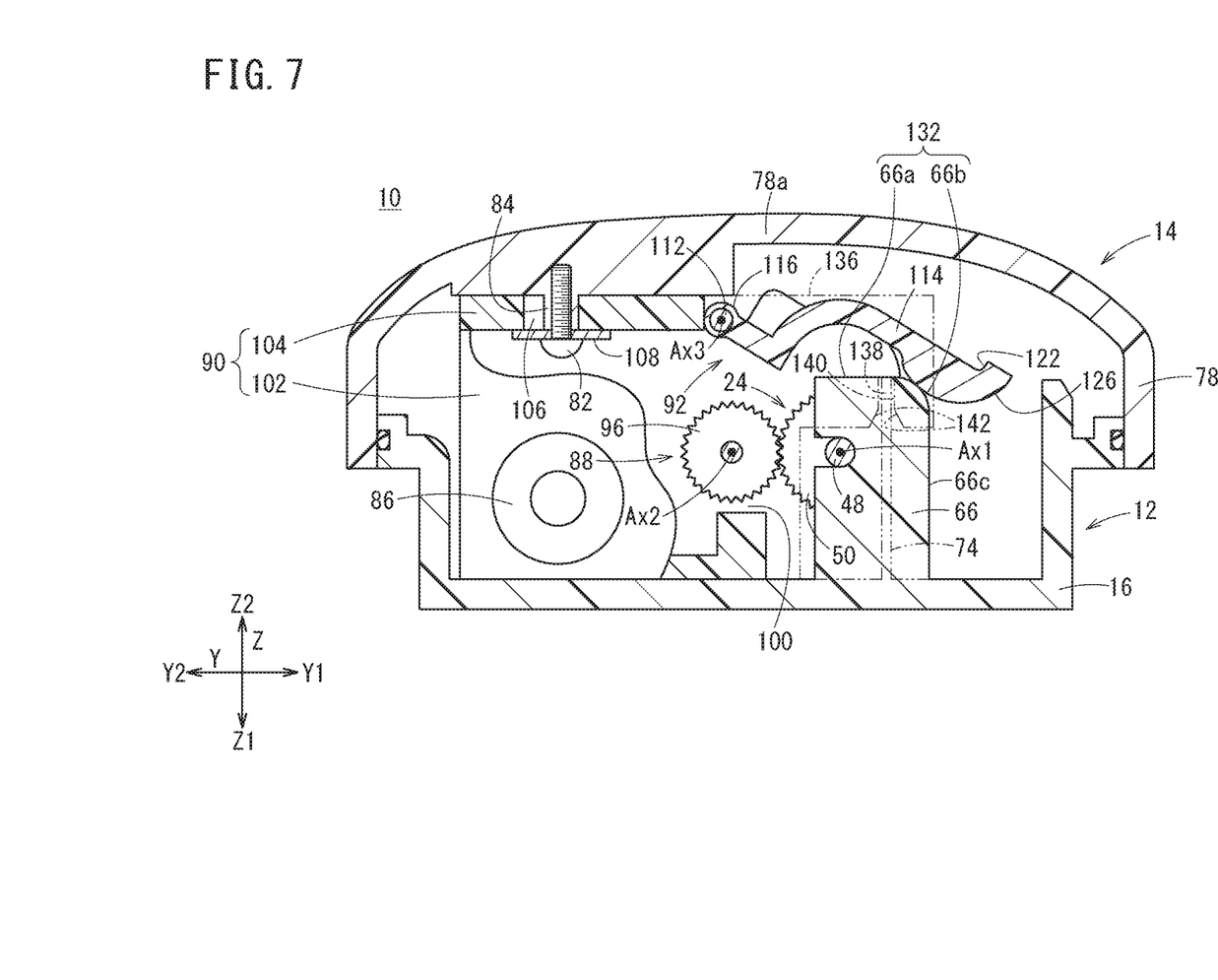
FIG. 7 is a partially omitted cross-sectional view of the disposable part completely attached to the reusable part.

The housing 90 is adjacently located in the Y2 direction from the bearing 66 in the attached state (see FIG. 7). The housing 90 includes a first casing member 102, where the opening part 100 for partially exposing the output gear 96 is formed, and a second casing member 104 attached to the first casing member 102. The second casing member 104 is provided with a plurality (two in the examples shown in, for example, FIG. 3A) of hole parts 106 into which the boss 84 of the cover body 78 can be inserted.

The hole part 106 is a long hole extending along the Y direction (aligning direction of the input gear 50 and the output gear 96 in the attached state). Accordingly, as seen in FIG. 4, a predetermined clearance along the Y direction is formed between the inner surface of the hole part 106 and the boss 84 when the boss 84 is inserted into the hole part 106. Moreover, the screw member 82 is screwed in the boss 84, which is inserted into the hole part 106 of the second casing member 104, through a washer 108 in contact with the inner surface of the second casing member 104. In this manner, the housing 90 is mounted on the cover body 78 while being movable along the Y direction.

The cover part 92 is provided openably/closably at the opening part 100 of the first casing member 102. The cover part 92 includes a shaft 112 and a cover part main body 114. The shaft 112 is provided in a groove 110 of the second casing member 104. The cover part main body 114 is rotatably provided on the shaft 112 and is capable of blocking the opening part 100. The shaft 112 is located on the side closer to the attachment part 78a than the opening part 100. An axis Ax3 of the shaft 112 is located on, in the aligning direction (Y direction), the side opposite to the input gear 50 (Y2 direction) in the attached state with respect to the rotation axis Ax2 of the output gear 96.

The cover part main body 114 includes a tubular part 116, a plate part 118, a circular arc part 120, and an extension part 122. The tubular part 116 has an internal hole into which the shaft 112 is inserted. The plate part 118 is extended from the tubular part 116 in a straight line. The circular arc part 120 is formed on the distal-end part of the plate part 118 while being extended in substantially a semicircular arc shape along the output gear 96. The extension part 122 is extended from the X1-direction end part of the circular arc part 120 to the side opposite to the tubular part 116.

The distal-end surface of the circular arc part 120 is in contact with a first region 124 of the outer surface of the first casing member 102 when the cover part 92 is in the closed state. The extension part 122 has a longitudinal section shape as if a complete circle is cut along a chord shorter than its diameter. The extension part 122 has an arc-like curved surface 126 on the interior side, and a flat surface 128 on the exterior side. The curved surface 126 is in contact with a second region 130 of the outer surface of the first casing member 102, which is positioned in the Y1 direction with respect to the first region 124 when the cover part 92 is in the closed state.

More specifically, in the closed state, the wall surface of the housing 90 (first region 124 and second region 130) keeps on pushing the cover part 92 by the pushing force of the pushing member 94. Therefore, adhesion of foreign matter onto the output gear 96 can be securely inhibited when the disposable part 12 is unattached to the reusable part 14.

Moreover, a portion of the extension part 122 that contacts the contact part 132 first at the time of attaching the disposable part 12 to the reusable part 14 (distal-end part 126a of the extension part 122) is located on, in the attached state, the same side where the input gear 50 is located (Y1 direction) with respect to the rotation axis Ax2 of the output gear 96. Note that the distal-end part 126a of the extension part 122 protrudes outward from the flat surface 128.

As shown in FIGS. 3A and 3B, the pushing member 94 pushes the cover part 92 into the closed state, while being configured as a torsion spring 95 that includes a coil 95a and a pair of extended end parts 95b and 95c extending from the coil 95a. The shaft 112 is provided in the internal hole of the coil 95a. The extended end part 95b is locked to the second casing member 104, and the other extended end part 95c is locked to the outer surface of the plate part 118 constituting the cover part main body 114. In this manner, the configuration of the pushing member 94 can be simplified because the pushing member 94 is configured as the torsion spring 95 according to the present embodiment.

However, the pushing member 94 may be constituted by spring members other than the torsion spring, rubber members, or the like. In other words, the pushing member 94 may employ any configuration as long as pushing force can be applied to the cover part 92 so that the cover part 92 is pushed to become the closed state.

In the driving part 80 like this, the distal-end surface 66a and the curved surface 66b of the bearing 66 of the disposable part 12 (the distal-end surface 66a and the curved surface 66b are collectively called the contact part 132) contact the cover part 92 formed on the reusable part 14, at the time of attaching the disposable part 12 to the reusable part 14. Subsequently, the cover part 92 opens toward the side where the attachment part 78a is located and is maintained in the opened state while resisting the pushing force of the pushing member 94 (see FIGS. 4 to 7). When the disposable part 12 is detached from the reusable part 14, the cover part 92 moves such that the opening part 100 is blocked by the pushing force of the pushing member 94, and the cover part 92 enters the closed state. More specifically, the cover part 92 automatically shifts from the closed state to the opened state when the disposable part 12 is attached to the reusable part 14, while automatically shifts from the opened state to the closed state by the pushing force of the pushing member 94 when the disposable part 12 is detached from the reusable part 14.

As shown in FIGS. 3A to 4, the driving part 80 further includes an arm part 134 and a protrusion part 136. The arm part 134 is formed such that the second casing member 104 is extended in the Y1 direction (side where the bearing 66 is located in the attached state) from a region adjacent to the cover part 92 in the X1 direction. The protrusion part 136 protrudes in the Z1 direction (direction opposite to the attachment part 78a) from the end part of the arm part 134 in the X2 direction. The protrusion part 136 is extended along the Y direction throughout the whole length of the arm part 134. That is, the protrusion part 136 is integrally formed with respect to the second casing member 104.

A distal-end surface (Z1-direction end surface) of the protrusion part 136 is provided with a positioning recess part (reusable-side positioning part) 140, in which a positioning projection part (disposable-side positioning part) 138 as a distal-end part of the first wall 74 of the disposable part 12 can be inserted (engaged).

Figure 6A:
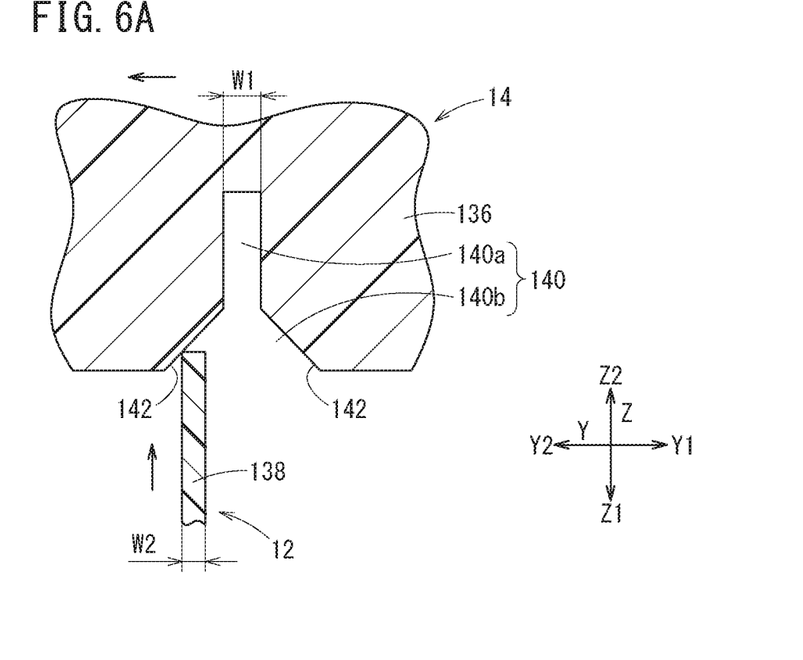
FIG. 6A is a first explanatory view explaining a positioning action of the medicinal-liquid administering device of FIG. 5.

The positioning recess part 140 is provided to position the output gear 96 of the reusable part 14 in an appropriate meshing position to be meshed with the input gear 50 of the disposable part 12, in corporation with the positioning projection part 138, at the time of attaching the disposable part 12 to the reusable part 14. The positioning recess part 140 is a hole (slit) opened on both sides in the X direction of the protrusion part 136. As shown in FIG. 6A, the positioning recess part 140 includes a position fixing part 140a and a guiding part 140b. An opening width of the position fixing part 140a (opening dimension in the Y direction) is constant (opening width W1) from the bottom surface to the intermediate position in the Z direction. An opening width of the guiding part 140b is gradually widened in the Z1 direction, from the intermediate position toward the opening part in the Z1 direction.

Specifically, the guiding part 140b includes taper surfaces 142 formed on the end parts in the Z1 direction of the opposing walls constituting the positioning recess part 140. The opening width of the positioning recess part 140 is gradually widened in the Z1 direction. The opening width W1 of the positioning recess part 140 is similar to or slightly wider than a width W2 of the positioning projection part 138 (see FIG. 6A).

In the reusable part 14 like this, a movable range of the housing 90 is set such that the positioning projection part 138 and the positioning recess part 140 face each other when the disposable part 12 is attached to the reusable part 14.

The medicinal-liquid administering device 10 according to the present embodiment is basically configured in the above-described manner, and operations and working effects thereof will be described next.

First, the user takes out the disposable part 12 from a packaging container. In this state, the tubular body 20 of the disposable part 12 is not filled with the medicinal liquid, and the nut part 46 is at the initial position that is not in contact with the plunger 22 (see FIG. 2). Note that the cover part 92 of the reusable part 14 in the initial state is maintained in the closed state by the pushing force of the pushing member 94. Therefore, adhesion of foreign matter such as grit and dust onto the reusable-side power transmission part 88 (output gear 96), which is housed in the housing 90, can be inhibited.

Then, the user adjusts the position of the plunger 22 with respect to the tubular body 20 within the disposable part 12, and fills the tubular body 20 with an appropriate amount of medicinal liquid from a medicinal liquid container such as a vial in which the medicinal liquid is stored in a hermetically sealed manner. The user then attaches the disposable part 12 to the reusable part 14. Specifically, the user brings the reusable part 14 and the disposable part 12 close to each other in the Z direction to join the parts together.

Figure 5:
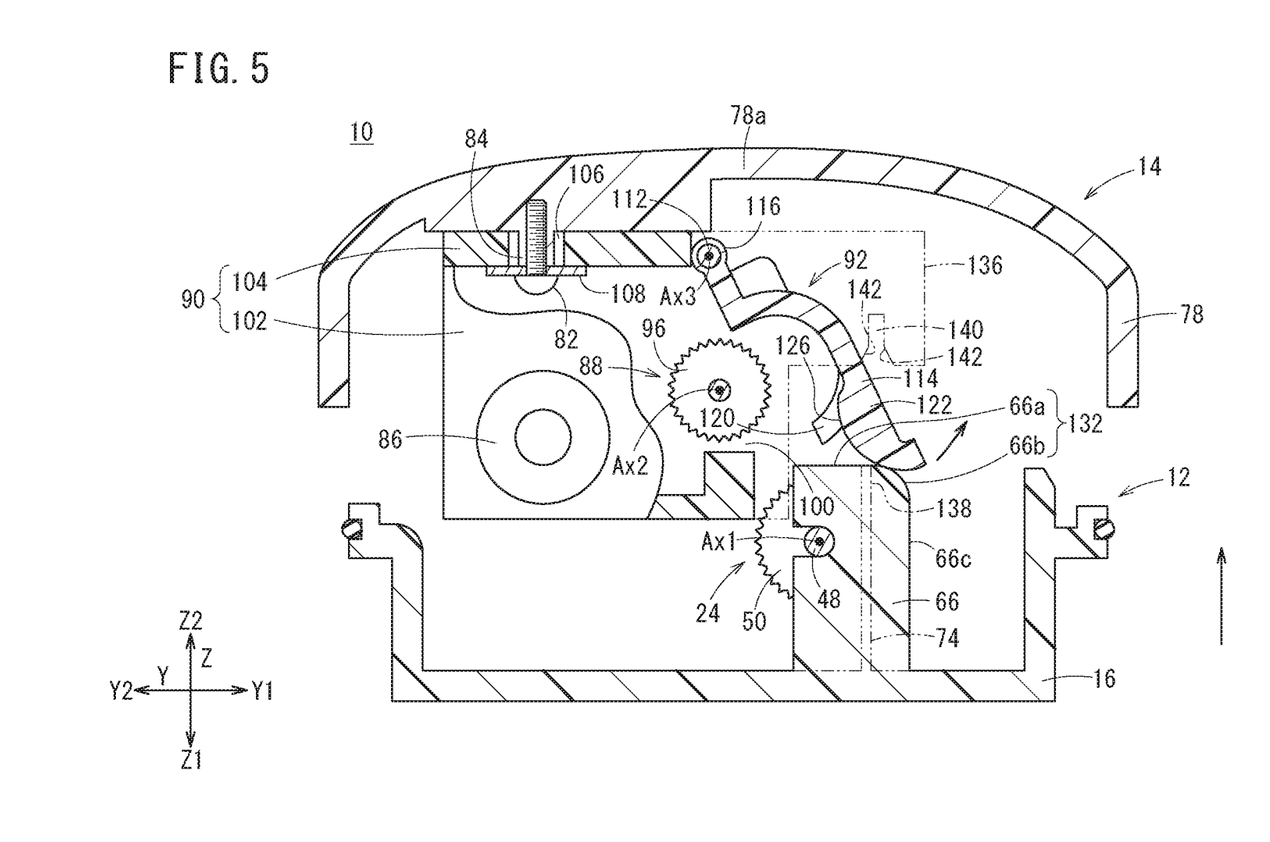
FIG. 5 is a partially omitted cross-sectional view of the cover part of FIG. 4 starting to open.

As shown in FIG. 4, the distal-end part 126*a* of the extension part 122 of the cover part 92, formed on the reusable part 14, contacts the distal-end surface 66*a* (contact part 132) of the bearing 66, formed on the disposable part 12, at the beginning of joining the reusable part 14 and the disposable part 12. Then, as shown in FIG. 5, when the reusable part 14 and the disposable part 12 continue to be brought close to each other, the curved surface 126 of the cover part 92 slides on the distal-end surface 66*a* of the bearing 66, formed on the disposable part 12, in the Y1 direction so that the cover part 92 rotates on the shaft 112 while resisting the pushing force of the pushing member 94. In other words, the cover part 92 starts to open.

When the reusable part 14 and the disposable part 12 further continue to be brought close to each other, the curved surface 126 of the cover part 92 contacts the curved surface 66*b* of the bearing 66 so that the cover part 92 opens further, making a part of the output gear 96 exposed outside of the housing 90 via the opening part 100.

Figure 6B:
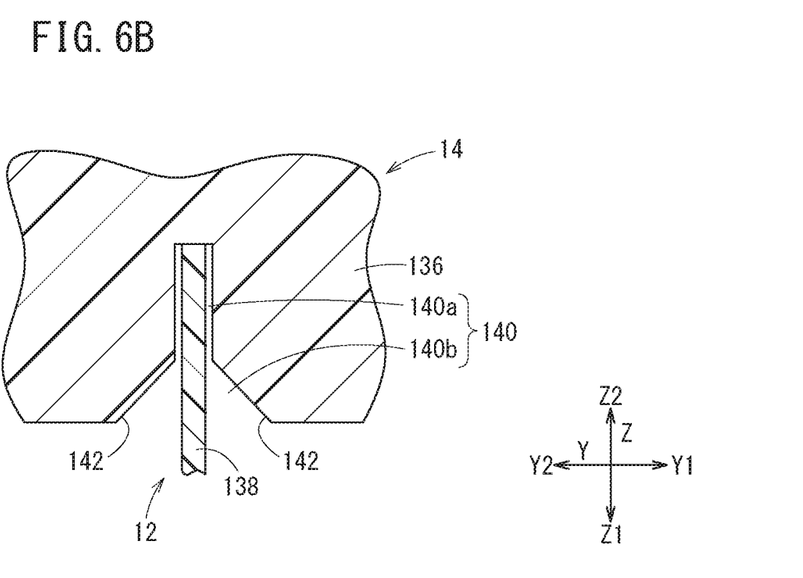
FIG. 6B is a second explanatory view further explaining the positioning action.

In association with the joining operation of the reusable part 14 and the disposable part 12, the positioning projection part (disposable-side positioning part) 138 is inserted into the positioning recess part (reusable-side positioning part) 140. Specifically, as shown in FIGS. 6A to 7, the positioning projection part 138 contacts one of the taper surfaces 142 of the guiding part 140*b* so that the taper surface 142 is pushed by the positioning projection part 138 in the Y direction (Y2 direction in the example of FIG. 6A). The housing 90 thus relatively moves in the Y direction with respect to the cover body 78 and the disposable part 12, and the positioning projection part 138 is inserted into the position fixing part 140*a*. Accordingly, the output gear 96 is positioned in the Y direction relative to the input gear 50.

Subsequently, the reusable part 14 and the disposable part 12 are joined to be integrated. At this time, the curved surface 126 of the cover part 92 contacts the curved surface 66*b*(contact part 132) of the bearing 66, thereby maintaining the cover part 92 in the opened state. The output gear 96 is thus securely meshed with the input gear 50 at the appropriate meshing position (engaging position). Therefore, the driving force of the reusable-side power transmission part 88 can be transmitted to the disposable-side power transmission part 24 effectively. Moreover, the motor 86 of the reusable part 14 is electrically coupled to the battery 26 of the disposable part 12 because the reusable part 14 and the disposable part 12 are joined together.

The user carries out priming of the medicinal-liquid administering device 10 after the reusable part 14 is joined to the disposable part 12 with the tubular body 20 filled with the medicinal liquid, thereby filling the whole discharging path for the medicinal liquid from the tubular body 20 through the lumen of the lead-out tube 32. First, the nut part 46 advances, from the initial position where the plunger 22 is not in contact therewith, to engage with the plunger 22. Then, the nut part 46 further advances, whereby the plunger 22 advances inside the tubular body 20 to discharge the medicinal liquid. Specifically, a remote controller (not shown) is operated to rotationally drive the motor 86. As a result, the rotary driving force of the motor 86 is transmitted to the reusable-side power transmission part 88 and the disposable-side power transmission part 24. Therefore, the feed screw shaft 44 is rotated, and the nut part 46 advances from the initial position toward the plunger 22 while sliding on the guide wall 64 (see FIGS. 1 and 2).

In more detail, the nut part 46 advances, by the rotary drive of the motor 86, to reach the distal-end side of the plunger 22 when the nut part 46 is engaged with the plunger 22. The pair of claw parts 42 then abuts the wall surfaces constituting the through holes 60 of the nut part 46, and the pair of leg parts 40 is warped to get close to each other. Then, when the claw parts 42 go through the through holes 60, the claw parts 42 return to the original positions, thereby locking the nut part 46 with respect to the plunger 22. As a result, the nut part 46, when advancing, can press the plunger 22 to advance inside the tubular body 20 to the distal-end direction. When the nut part 46 is caused to further advance by the rotary drive of the motor 86, the medicinal liquid in the tubular body 20 is pressed by the plunger 22 so that the medicinal liquid is discharged from the lumen of the lead-out tube 32. In this way, the medicinal liquid is pressed by driving the motor 86 and the whole discharging path for the medicinal liquid is filled with the medicinal liquid, thereby completing the priming.

Subsequently, the user pastes the cradle (not shown) at a site of the skin for injecting the medicinal liquid. As described above, the cradle can be attached/detached to/from the base part 16 of the disposable part 12, and includes the needling mechanism. The living body is punctured by using the needling mechanism, and the cannula mechanism 18 is fixed to the cradle while the cannula is indwelled in the living body. When the disposable part 12 joined to the reusable part 14 is attached to the cradle thereafter, the lead-out tube 32 formed on the disposable part 12 communicates with the cannula mechanism 18 formed on the cradle. As described above, when the medicinal-liquid administering device 10 is pasted to the user's skin, the tubular body 20 containing the medicinal liquid, which is formed on the reusable part 14, communicates with the inside of the living body from the cradle, through the lead-out port 30, the lead-out tube 32, the cannula mechanism 18, and the cannula. Moreover, the reusable-side power transmission part 88 and the disposable-side power transmission part 24 are configured to transmit the driving force. Furthermore, the motor 86 provided on the reusable part 14 is electrically joined to the battery provided on the disposable part 12. Thus, the medicinal liquid stored in the tubular body 20 is continuously or intermittently administered into the living body by driving the motor 86 to press the plunger 22.

When the medicinal liquid administration is completed, the user detaches the joining the disposable part 12 and the reusable part 14 from the cradle, and then separates the disposable part 12 from the reusable part 14. The cover part 92 formed on the reusable part 14 is then automatically closed by the pushing force of the pushing member 94. As a result, adhesion of foreign matter onto the output gear 96 (reusable-side power transmission part 88) can be inhibited.

According to the present embodiment, because the openable/closable cover part 92 is provided at the opening part 100 of the housing 90 that houses the reusable-side power transmission part 88, adhesion of foreign matter onto the reusable-side power transmission part 88 can be inhibited when the reusable part 14 and the disposable part 12 are not joined together.

Moreover, when the disposable part 12 is attached to the reusable part 14, the cover part 92 contacts the contact part 132 to be opened while resisting the pushing force of the pushing member 94, and maintains the opened state. Accordingly, the user is not required to hold the cover part 92 in the opened state with fingers or the like, at the time of attaching the reusable part 14 to the disposable part 12. The input gear 50 can be therefore easily and securely meshed (engaged) with the output gear 96 without the need of complicated work.

Furthermore, because the cover part 92 is automatically closed by the pushing force of the pushing member 94 at the time of detaching the disposable part 12 from the reusable part 14, the user is not required to close the cover part 92 with fingers or the like. Therefore, adhesion of foreign matter onto the reusable-side power transmission part 88 can be inhibited without the need of complicated work.

In the present embodiment, the cover part 92 includes the shaft 112 formed on the second casing member 104 and the cover part main body 114 that is rotatably provided on the shaft 112 and is capable of blocking the opening part 100 of the first casing member 102. Moreover, the pushing member 94 pushes the cover part 92 into the closed state by applying the pushing force to the cover part main body 114 along the circumferential direction of the shaft 112. Therefore, the cover part 92 can be pushed to become the closed state with a simple configuration.

In the present embodiment, the shaft 112 is located on the side closer to the attachment part 78a than the opening part 100 of the housing 90. The cover part 92 opens toward the attachment part 78a side when the disposable part 12 is attached to the reusable part 14. Accordingly, the cover part 92 can be securely opened at the time of attaching the disposable part 12 to the reusable part 14.

Moreover, the axis Ax3 of the shaft 112 (rotation axis of the cover part 92) is located in the Y2 direction with respect to the rotation axis Ax2 of the output gear 96. A portion of the cover part 92 that contacts the contact part 132 first (distal-end part 126a of the extension part 122) is located in the Y1 direction with respect to the rotation axis Ax2 of the output gear 96. Accordingly, the cover part 92 can be easily opened at the time of attaching the disposable part 12 to the reusable part 14.

In the present embodiment, the disposable part 12 can be simply configured because the contact part 132 is provided on the bearing 66 of the disposable part 12.

The medicinal-liquid administering device 10 according to the present embodiment is not limited to the configurations described above. For example, the contact part 132 may be provided on the bearing 68 or the side wall of the base part 16. The cover part 92 is not limited to the configuration in which the cover part main body 114 rotates with respect to the shaft 112 to open/close the cover part 92, but can be other configurations. For example, the cover part 92 may be opened/closed by sliding in the X direction. The battery 26 may be provided on the reusable part 14 instead of the disposable part 12.

Moreover, the cover part 92 may be configured such that the shaft 112 is rotatably provided with respect to the housing 90, and also the tubular part 116 is secured to the shaft 112. Furthermore, the axis Ax3 of the shaft 112 may be, in the Y direction, at the same position as the rotation axis Ax2 of the output gear 96.

It is apparent that the medicinal-liquid administering device according to the present invention is not limited to the embodiments described above and can employ various configurations without departing from the gist of the present invention.

What is claimed is:

1. A device comprising:
a first member comprising:
a driving source that is configured to provide a driving force for pressing a pressing member toward a medicinal liquid to administer the medicinal liquid,
a first-member-side power transmission part configured to receive the driving force from the driving source for pressing the pressing member,
a housing covering the first-member-side power transmission part, the housing comprising an opening part configured such that the first-member-side power transmission part is partially exposed from the housing at the opening part,
an openable and closable cover part located at the opening part and rotatably mounted on the housing via a shaft,
a pushing member configured to push the cover part into a closed state by applying a pushing force to the cover part along a circumferential direction of the shaft, and
an attachment part to which the housing is attached, the attachment part covering the second member,
wherein the shaft is located on a side closer to the attachment part than to the opening part; and
a second member comprising a second-member-side power transmission part configured to be attachable to and detachable from the first member, the second member being a part of a medicinal-liquid administering device;
wherein, when the first member is attached to the second member, the second member opens the cover part toward an attachment part side to engage the second-member-side power transmission part with the first-member-side power transmission part, for administering the medicinal liquid into a living body.

2. The device according to claim 1, wherein the pushing member comprises a torsion spring.

3. The device according to claim 1, wherein:
the first-member-side power transmission part comprises an output gear configured to rotate due to the driving force from the driving source;
the output gear is partially exposed from the housing via the opening part when the cover part is in an opened state; and
the second-member-side power transmission part comprises an input gear configured to mesh with the output gear.

4. The device according to claim 3, wherein:
the second-member-side power transmission part comprises:
a rotation shaft that is coaxially provided relative to the input gear,
a bearing that rotatably supports the rotation shaft, and
a contact part configured to contact the cover part is located on the bearing.

5. The device according to claim 3, wherein the input gear comprises a first spur gear, and the output gear comprises a second spur gear.

6. The device according to claim 1, wherein:
the cover part automatically shifts from the closed state to an opened state when the second member is attached to the first member; and
the cover part automatically shifts from the opened state to the closed state by the pushing force of the pushing member when the second member is detached from the first member.

7. The device according to claim 1, wherein the cover part comprises:
a tubular part;
a plate part;
a circular arc part; and
an extension part;
wherein the tubular part comprises an internal hole into which the shaft is inserted,
wherein the plate part extends from the tubular part in a straight line,
wherein the circular arc part is formed on a distal end part of the plate part and extends in substantially a semi-circular arc shape, and
wherein the extension part extends from an end part of the circular arc part to a side opposite the tubular part.

8. The device according to claim 7, wherein the extension part has an arc-like curved surface on an interior side, and a flat surface on an exterior side.

9. A method comprising:
providing a first member comprising:
a driving source that is configured to provide a driving force for pressing a pressing member toward a medicinal liquid to administer the medicinal liquid,
a first-member-side power transmission part configured to receive the driving force from the driving source for pressing the pressing member,
a housing covering the first-member-side power transmission part, the housing comprising an opening part configured such that the first-member-side power transmission part is partially exposed from the housing at the opening part,
an openable and closable cover part located at the opening part and rotatably mounted on the housing via a shaft,
a pushing member configured to push the cover part into a closed state by applying a pushing force to the cover part along a circumferential direction of the shaft, and
an attachment part to which the housing is attached, the attachment part covering the second member,
wherein the shaft is located on a side closer to the attachment part than to the opening part; and
providing a second member comprising a second-member-side power transmission part configured to be attachable to and detachable from the first member, the second member being a part of a medicinal-liquid administering device;
attaching the first member to the second member, whereby the second member opens the cover part toward an attachment part side, and the second-member-side power transmission part engages with the first-member-side power transmission part for administering the medicinal liquid into a living body.

10. The method of claim 9, wherein:
the first-member-side power transmission part comprises an output gear configured to rotate due to the driving force from the driving source;
the output gear is partially exposed from the housing via the opening part when the cover part is in an opened state; and
the second-member-side power transmission part comprises an input gear configured to mesh with the output gear.

11. The method of claim 10, wherein the second-member-side power transmission part comprises:
a rotation shaft that is coaxially provided relative to the input gear,
a bearing that rotatably supports the rotation shaft, and
a contact part configured to contact the cover part is located on the bearing.

12. The method of claim 11, wherein:
in the step of attaching the first member to the second member, the cover part is opened by:
contacting a top surface of the contact part with an interior surface of a circular arc part of the cover part of the housing before the first member and the second member are engaged; and
sliding the interior surface of the circular arc part of the cover part along the top surface of the contact part in a direction that is perpendicular to an engagement direction, after the cover part of the housing contacts the top surface of the contact part and before the first member and the second member are engaged.

13. The method of claim 9, wherein the cover part comprises:
a tubular part;
a plate part;
a circular arc part; and
an extension part;
wherein the tubular part comprises an internal hole into which the shaft is inserted,
wherein the plate part extends from the tubular part in a straight line,
wherein the circular arc part is formed on a distal end part of the plate part and extends in substantially a semi-circular arc shape, and
wherein the extension part extends from an end part of the circular arc part to a side opposite the tubular part.

14. A method comprising:
providing a first member comprising:
a driving source that is configured to provide a driving force for pressing a pressing member toward a medicinal liquid to administer the medicinal liquid,
a first-member-side power transmission part configured to receive the driving force from the driving source for pressing the pressing member,
a housing covering the first-member-side power transmission part, the housing comprising an opening part configured such that the first-member-side power transmission part is partially exposed from the housing at the opening part,
an openable and closable cover part located at the opening part and rotatably mounted on the housing via a shaft, and
a pushing member configured to push the cover part into a closed state by applying a pushing force to the cover part along a circumferential direction of the shaft; and
providing a second member comprising a second-member-side power transmission part configured to be attachable to and detachable from the first member, the second member being a part of a medicinal-liquid administering device;

attaching the first member to the second member such that the second member automatically shifts the cover part from the closed state to an opened state to engage the second-member-side power transmission part with the first-member-side power transmission part, for administering the medicinal liquid into a living body; and detaching the first member from the second member such that the cover part automatically shifts from the opened state to the closed state by the pushing force of the pushing member.

15. A device comprising:
a first member comprising:
   a driving source that is configured to provide a driving force for pressing a pressing member toward a medicinal liquid to administer the medicinal liquid,
   a first-member-side power transmission part configured to receive the driving force from the driving source for pressing the pressing member,
   a housing covering the first-member-side power transmission part, the housing comprising an opening part configured such that the first-member-side power transmission part is partially exposed from the housing at the opening part,
   an openable and closable cover part located at the opening part and rotatably mounted on the housing via a shaft, and
   a pushing member configured to push the cover part into a closed state by applying a pushing force to the cover part along a circumferential direction of the shaft; and
a second member comprising a second-member-side power transmission part configured to be attachable to and detachable from the first member, the second member being a part of a medicinal-liquid administering device;
wherein, when the first member is attached to the second member, the second member is configured to automatically shift the cover part from the closed state to an opened state to engage the second-member-side power transmission part with the first-member-side power transmission part, for administering the medicinal liquid into a living body;
wherein, when the first member is detached from the second member, the cover part automatically shifts from the opened state to the closed state by the pushing force of the pushing member.

16. The device according to claim 15, wherein the pushing member comprises a torsion spring.

17. The device according to claim 15, wherein:
the first-member-side power transmission part comprises an output gear configured to rotate due to the driving force from the driving source;
the output gear is partially exposed from the housing via the opening part when the cover part is in the opened state; and
the second-member-side power transmission part comprises an input gear configured to mesh with the output gear.

18. The device according to claim 17, wherein:
the second-member-side power transmission part comprises:
   a rotation shaft that is coaxially provided relative to the input gear, and
   a bearing that rotatably supports the rotation shaft, and
   a contact part configured to contact the cover part is located on the bearing.

19. The device according to claim 17, wherein the input gear comprises a first spur gear, and the output gear comprises a second spur gear.

20. The device according to claim 15, wherein:
the cover part automatically shifts from the closed state to an opened state when the second member is attached to the first member; and
the cover part automatically shifts from the opened state to the closed state by the pushing force of the pushing member when the second member is detached from the first member.

21. The device according to claim 15, wherein the cover part comprises:
   a tubular part;
   a plate part;
   a circular arc part; and
   an extension part;
   wherein the tubular part comprises an internal hole into which the shaft is inserted,
   wherein the plate part extends from the tubular part in a straight line,
   wherein the circular arc part is formed on a distal end part of the plate part and extends in substantially a semi-circular arc shape, and
   wherein the extension part extends from an end part of the circular arc part to a side opposite the tubular part.

22. The device according to claim 21, wherein the extension part has an arc-like curved surface on an interior side, and a flat surface on an exterior side.

* * * * *